United States Patent

Takaoka et al.

Patent Number: 5,171,651
Date of Patent: Dec. 15, 1992

[54] ELECTROPHOTOGRAPHIC PHOTORECEPTOR WITH A CARRIER TRANSPORT LAYER CONTAINING A HYDROQUINONE COMPOUND

[75] Inventors: Kazuchiyo Takaoka; Makoto Okaji; Hideya Arisue, all of Tsukuba, Japan

[73] Assignee: Mitsubishi Paper Mills Limited, Tsukuba, Japan

[21] Appl. No.: 610,578

[22] Filed: Nov. 8, 1990

[30] Foreign Application Priority Data

Nov. 13, 1989 [JP] Japan .................................. 1-294151

[51] Int. Cl.$^5$ .................................................. G03G 5/10
[52] U.S. Cl. ........................................ 430/59; 430/58; 430/73; 430/76
[58] Field of Search ................... 430/58, 59, 72, 73, 430/74, 75, 76, 77

[56] References Cited

U.S. PATENT DOCUMENTS 4,975,350  12/1990  Fujimaki et al. ...................... 430/59

OTHER PUBLICATIONS

German Patent Office Official Action and translation thereof, dated Dec. 4, 1991; No P4036094 6-51.
Chem. Abstract No. CA 112 (4): 28130x.

*Primary Examiner*—Marion E. Mc Camish
*Assistant Examiner*—S. Rosasco
*Attorney, Agent, or Firm*—Cushman, Darby & Cushman

[57] ABSTRACT

Disclosed is a double-layered type electrophotographic photoreceptor which comprises an electroconductive support and a carrier generation layer containing a pigment or a dye as a carrier generation material and a carrier transport layer which are provided on said support, wherein the carrier transport layer contains an organic low molecular weight carrier transport material, a binder resin, a hydroquinone compound represented by the following formula (II):

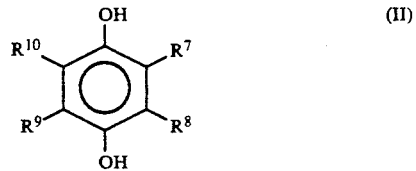

wherein $R^7$, $R^8$, $R^9$ and $R^{10}$ each represents a hydrogen atom, a halogen atom, an alkyl group, an aryl group, an alkoxy group, a carbamoyl group or an alkylthio group, and a compound represented by the following formula (III):

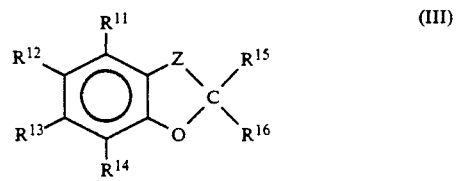

wherein $R^{11}$, $R^{12}$, $R^{13}$ and $R^{14}$ each represents a hydrogen atom, a hydroxyl group, an alkyl group or an alkoxy group with a proviso that at least one of $R^{11}$–$R^{14}$ is hydroxyl group, $R^{15}$ and $R^{16}$ each represents a hydrogen atom, an alkyl group or an alkenyl group and Z represents a group of atoms necessary to form a 2H-chromene skeleton, chroman skeleton or dihydrobenzofuran skeleton together with the benzene ring in the formula and the group of atoms may be further substituted.

6 Claims, No Drawings

ELECTROPHOTOGRAPHIC PHOTORECEPTOR WITH A CARRIER TRANSPORT LAYER CONTAINING A HYDROQUINONE COMPOUND

BACKGROUND OF THE INVENTION

The present invention relates to an electrophotographic photoreceptor and more particularly to a double-layered electrophotographic photoreceptor excellent in storage stability and repeated use characteristics.

Hitherto, as electrophotographic photoreceptors, there have been known those which have a photosensitive layer mainly composed of inorganic photoconductors such as selenium, zinc oxide and cadmium sulfide.

However, these are not necessarily satisfactory in sensitivity, heat stability, moisture resistance and endurance and especially, selenium and cadmium sulfide photoreceptors are limited in production and in handling because of their toxicity.

On the other hand, electrophotographic photoreceptor having a photosensitive layer mainly composed of organic photoconductive compounds have many merits that they are relatively easy in production, inexpensive, easy in handling, and generally superior to selenium photoreceptors in heat stability and recently attract attentions in this field.

As such organic photoconductive compounds, poly-N-vinylcarbazole is well known and electrophotographic photoreceptor having a photosensitive layer mainly composed of a charge transfer complex formed from the above poly-N-vinylcarbazole and a Lewis acid such as 2,4,7-trinitro-9-fluorenone is disclosed in Japanese Patent Kokoku No. 50-10496. However, this photoreceptor is not necessarily satisfactory in sensitivity, film-formability and endurance.

On the other hand, organic photoconductors of low molecular weight represented by hydrazones and pyrazolines have been proposed. Film-formability can be considerably improved by combining these organic photoconductors with suitable binders, but improvement of sensitivity and endurance is not sufficient.

Under the circumstances, recently there have been proposed double-layered type photoreceptors where carrier generating function and carrier transporting function are born on separate substances. Employing this structure has resulted in remarkable improvements in charging characteristics and sensitivity and has given photoreceptors having sensitivity close to that of inorganic photoreceptors such as Se by combination of a carrier generation layer comprising azo pigment having a high carrier generating ability with a carrier transport layer containing a carrier transport material of hydrazone type which has a high carrier transporting ability. As a result, now the photoreceptors mainly composed of organic photoconductive compounds of these types have began to be used in the fields of copying machines and printers.

Electrophotographic photoreceptors are subjected to repetition of process comprising charging, exposing and removing of charge in copying machine and variation of initial potential after charging and residual potential after removal of charge affects the image and so must be as small as possible.

However, electrophotographic photoreceptors made of organic materials suffer from the problems that a slight amount of impurity incorporates into the materials during preparation thereof, which causes increase of residual potential and that because of inferior stability of materials per se, air oxidation or photo-decomposition occurs and results in impurity which causes increase of residual potential or decrease of initial potential. These are problems in use which are difficult to control.

SUMMARY OF THE INVENTION

The object of the present invention is to provide an electrophotographic photoreceptor excellent in storage stability and improved in repeated use characteristics when used repeatedly in electrophotographic process.

As a result of intensive research conducted by the inventors, it has been found that the above object can be attained by containing a pigment or dye in a carrier generation layer as a carrier generation material and a compound represented by the following formula (II) and a compound represented by the following formula (III) in a carrier transport layer.

That is the present invention is a double-layered type electrophotographic photoreceptor which comprises an electroconductive support and a carrier generation layer containing a pigment or a dye as a carrier generation material and a carrier transport layer which are provided on said support, characterized in that the carrier transport layer contains an organic low molecular weight carrier transport material, a binder resin, a hydroquinone compound represented by the following formula (II):

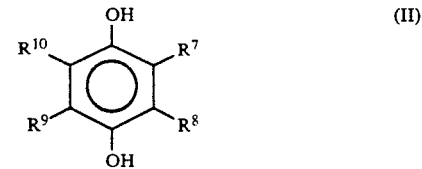

(wherein $R^7$, $R^8$, $R^9$ and $R^{10}$ each represents a hydrogen atom, a halogen atom, an alkyl group, an aryl group, an alkoxy group, a carbamoyl group, or an alkylthio group), and a compound represented by the following formula (III):

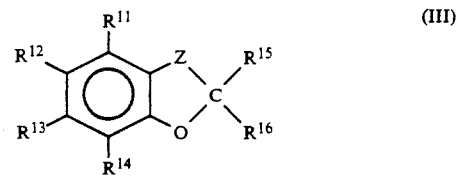

(wherein $R^{11}$, $R^{12}$, $R^{13}$ and $R^{14}$ each represent a hydrogen atom, a hydroxyl group, an alkyl group or an alkoxy group with a proviso that at least one of $R^{11}$-$R^{14}$ is hydroxyl group, $R^{15}$ and $R^{16}$ each represents a hydrogen atom, an alkyl group or an alkenyl group and Z represents a group of atoms necessary to form a 2H-chromene skeleton, chroman skeleton or dihydrobenzofuran skeleton together with the benzene ring in the formula and the group of atoms may be further substituted).

DESCRIPTION OF THE INVENTION

Respective constructive elements of the present invention will be explained below.

As conductive support on which a photosensitive layer is formed, there may be used any known supports which are employed for electrophotographic photoreceptors.

These supports include, for example, metallic drums and sheets of aluminum, copper and the like, laminates of these matallic foils and materials on which these metals are vapor deposited.

Moreover, there may be used plastic films, plastic drums and papers made electroconductive by coating with conductive materials such as metal powder, carbon black, copper iodide or polymeric electrolyte together with a suitable binder.

Further examples are plastic sheets or drums made conductive by containing conductive materials such as metal powder, carbon black and carbon fiber.

Carrier generation layer can be provided by coating a dispersion prepared by dispersing a pigment or a dye in a solvent together with a binder.

The pigment include, for example, azo pigments such monoazo pigments, polyazo pigments, metal complex azo pigment, pyrazolone azo pigments, and thiazole azo pigment; perylene azo pigments such as perylenic acid anhydride and perylenic acid imide; anthraquinone or polycyclic quinone pigments such as anthraquinone derivatives, anthanthrone derivatives, dibenzpyrenequinone derivatives, pyranthrone derivatives, violanthrone derivatives and isoviolanthrone derivatives; and phthalocyanine pigments such as metal phthalocyanine, metal naphthalocyanine, metal-free phthalocyanine, and metal-free naphthalocyanine. The dye used include, for example, triphenylmethane dyes such as Methyl Violet, quinone dyes such as quinizarin, pyrylium salts, thiapyrylium salts, and benzopyrylium salts.

The binder used include, for example, polymers and copolymers of vinyl compounds such as styrene, vinyl acetate, acrylic acid esters, and methacrylic acid esters, various polymers such as phenoxy resin, polysulfone, arylate resin, polycarbonate, polyester, cellulose ester, cellulose ether, urethane resin, epoxy resin, and acrylic polyol resin.

The solvent used include, for example, ethers such as 1,2-dimethoxyethane, tetrahydrofuran, and 1,4-dioxane; ketones such as methyl ethyl ketone and cyclohexanone; aromatic hydrocarbons such as toluene and xylene; aprotic polar solvents such as N,N-dimethylformamide, acetonitrile, N-methylpyrrolidone, and dimethyl sulfoxide; alcohols such as methanol, ethanol, and isopropanol; esters such as ethyl acetate, methyl acetate, and methylcellosolve acetate; and chlorinated hydrocarbons such as dichloroethane and chloroform.

The binder resin is used in an amount of about 1–400 parts by weight, preferably about 20–400 parts by weight per 100 parts by weight of pigment or dye. Thickness of carrier generation layer is preferably about 0.1–2.0 μ.

The carrier transport layer can be provided by dissolving a binder resin, an organic low-molecular weight carrier transport material and compounds represented by the formulas (II) and (III) in a suitable solvent and coating the solution.

As the binder, mention may be made of, for example, polymers and copolymers of vinyl compounds such as styrene, vinyl chloride, acrylic acid ester, methacrylic acid ester, and vinyl acetate, phenoxy resin, polysulfone, polycarbonate, polyarylate, polyester, cellulose ester, cellulose ether, urethane resin, epoxy resin, and silicone resin. Among them, polyarylate, polycarbonate and mixture of them are preferred.

As the solvent, there may be used tetrahydrofuran, methyl ethyl ketone, benzene, toluene, monochlorobenzene, 1,2-dichloroethane, methylene chloride, and ethyl acetate.

As the organic low-molecular carrier transport material, mention may be made of, for example, hydrazones, stilbens, oxadiazoles, triazoles, imidazoles, oxazoles, pyrazolines, triarylamines, benzoxazoles, and carbazoles. In view of the object of the present invention, among them, hydrazones and stilbenes are preferred, and especially preferred are hydrazones represented by the following formulas (I-a) and (I-b) and stilbenes represented by the following formula (IV).

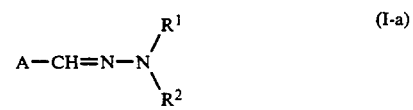

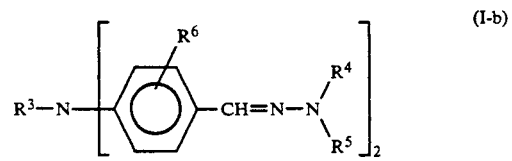

(wherein $R^1$, $R^2$, $R^3$, $R^4$, and $R^5$ each represents an alkyl, alkenyl, aralkyl, aryl or heterocyclic group which may be substituted, $R^6$ represents a hydrogen atom, an alkyl group, an alkoxy group or a halogen atom, and A represents an aromatic hydrocarbon or aromatic heterocyclic group which may have substituent.).

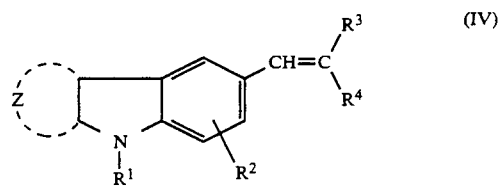

(wherein $R^1$, $R^2$, $R^3$, and $R^4$ each represent a hydrogen atom or an alkyl, aralkyl, or aryl group which may have substituent, $R^3$ and $R^4$ may link to each other to form a ring, and Z represents a group of atoms necessary to form a saturated 5-8 membered ring together with the two carbon atoms of indoline ring).

The stilbenes represented by the above formula (IV) are mentioned in detail in U.S. Application Ser. No. 07/565239 filed by Itoh et al on Aug. 10, 1990 (of the same assignee as of the present application).

The carrier transport materials represented by the formula (I-a) and (I-b) and (IV) are used in an amount of 20–500 parts by weight, preferably 50–200 parts by weight based on 100 parts by weight of the binder resin.

Examples of the hydrazones represented by the formulas (I-a) and (I-b) are shown below, but the present invention is never limited to use of them only.

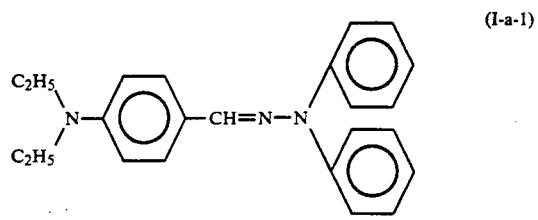

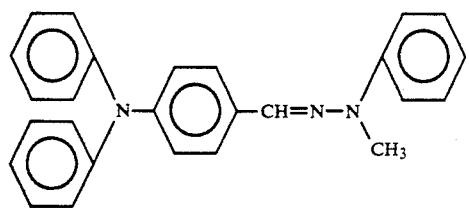 (I-a-2)
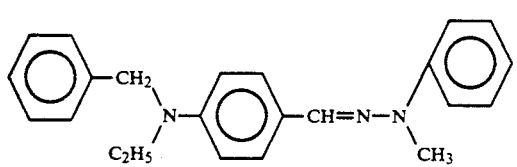 (I-a-3)
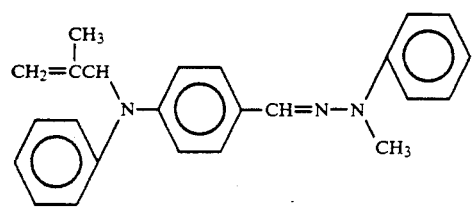 (I-a-4)
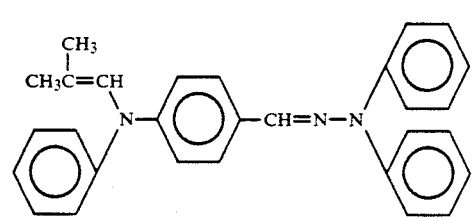 (I-a-5)
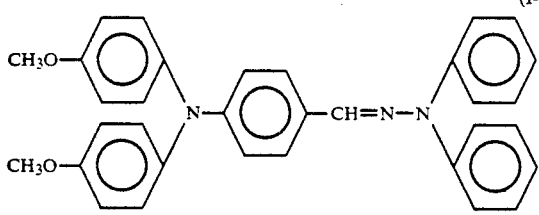 (I-a-6)
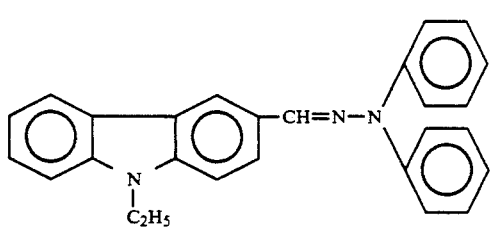 (I-a-7)
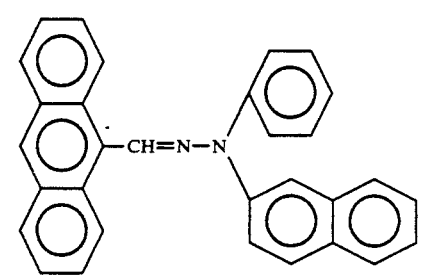 (I-a-8)
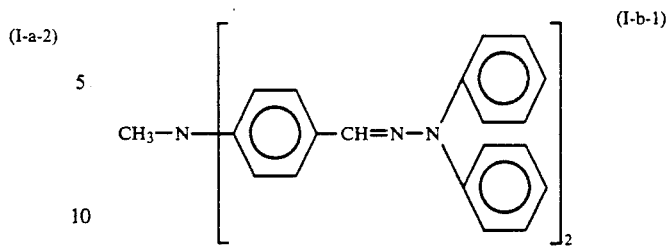 (I-b-1)
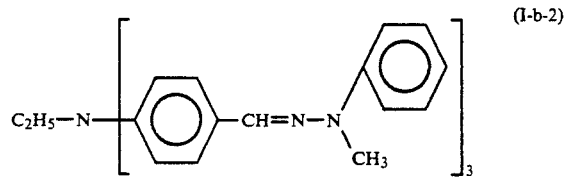 (I-b-2)
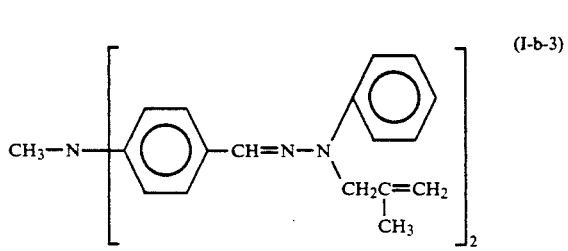 (I-b-3)
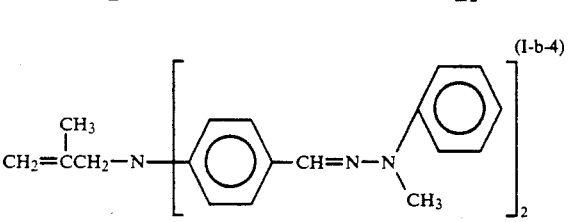 (I-b-4)
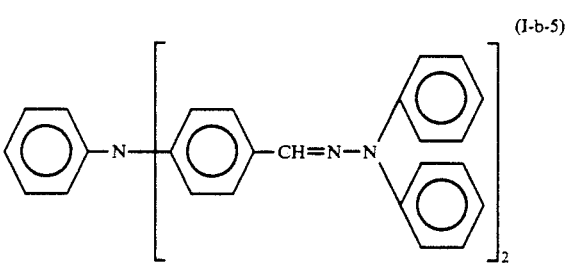 (I-b-5)
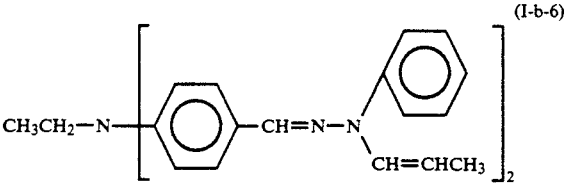 (I-b-6)
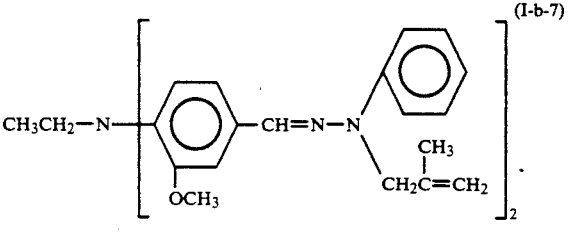 (I-b-7)
These compounds represented by the formulas (I-a) and (I-b) can be prepared by known process.

Examples of the stilbenes represented by the formula (IV) are shown below, but the present invention is never limited to use of them only.
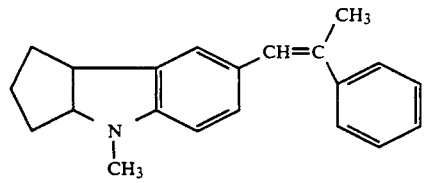 (IV-1)
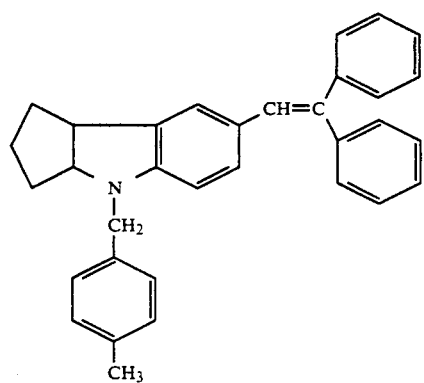 (IV-2)
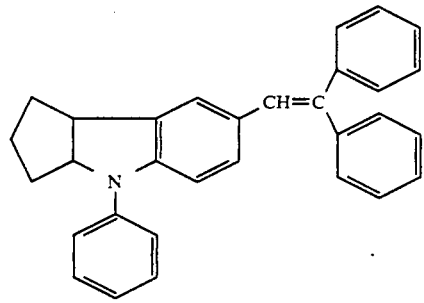 (IV-3)
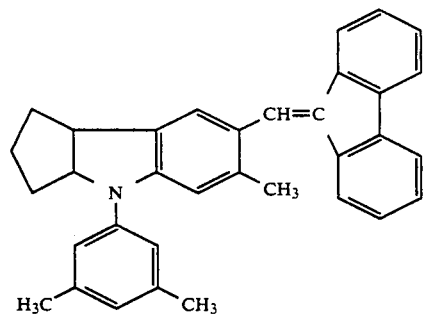 (IV-4)
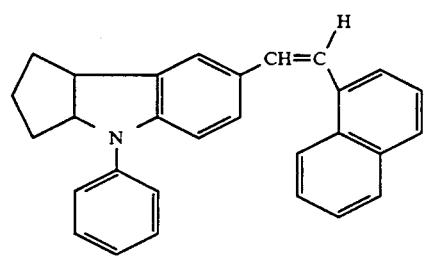 (IV-5)
-continued
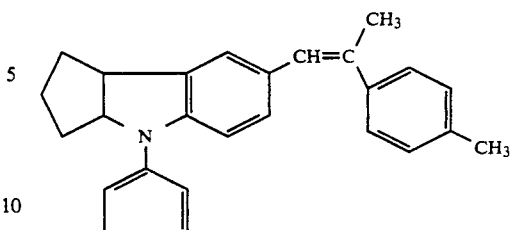 (IV-6)
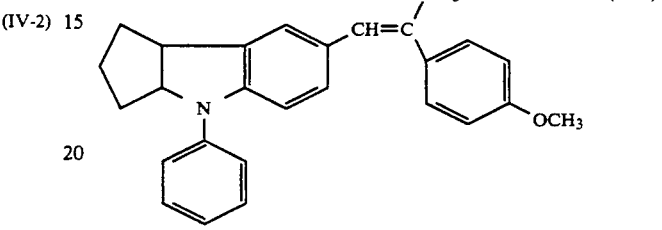 (IV-7)
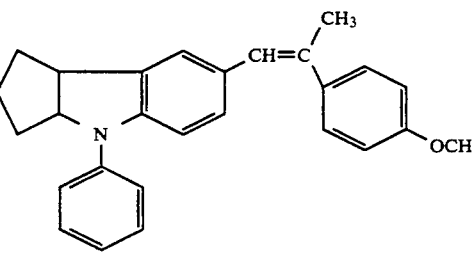 (IV-8)
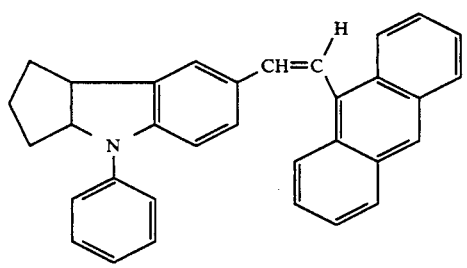 (IV-9)
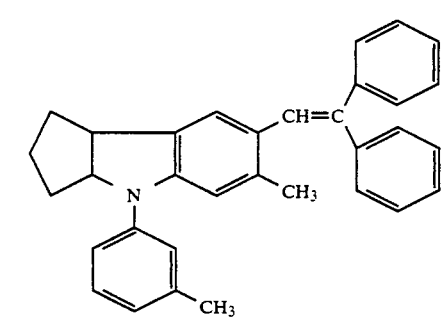 (IV-10)
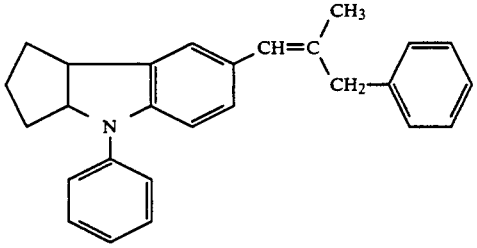 (IV-11)

-continued
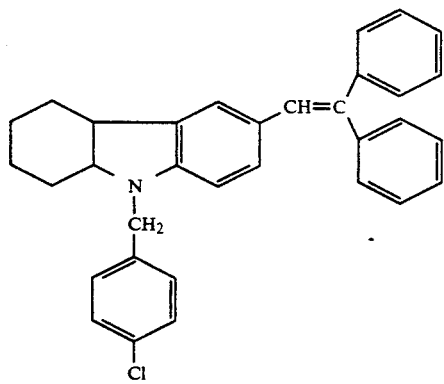 (IV-12)
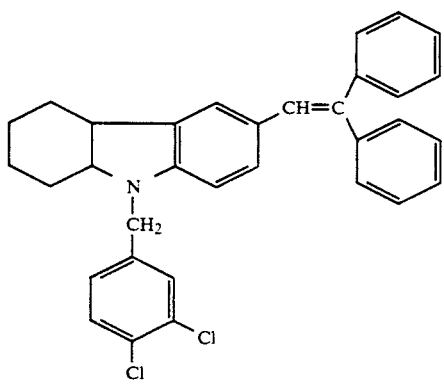 (IV-13)
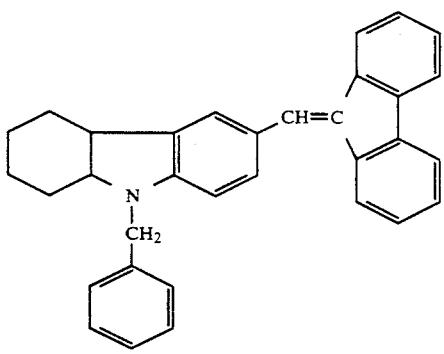 (IV-14)
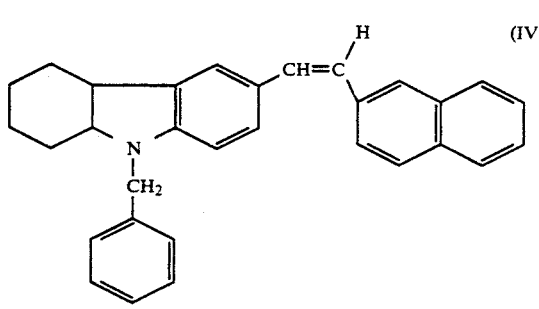 (IV-15)
-continued
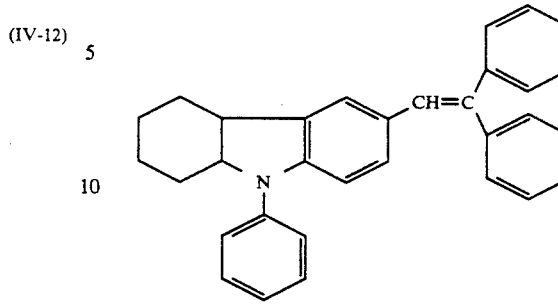 (IV-16)
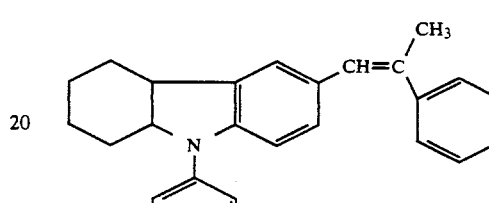 (IV-17)
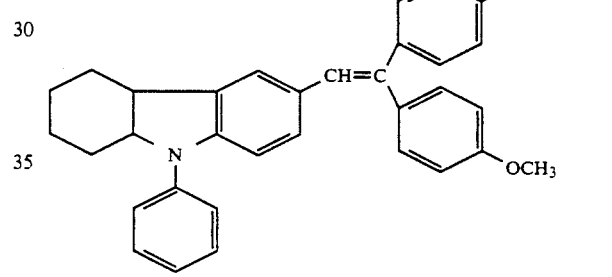 (IV-18)
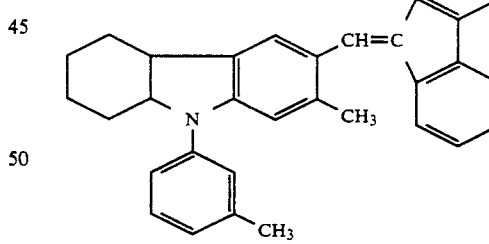 (IV-19)
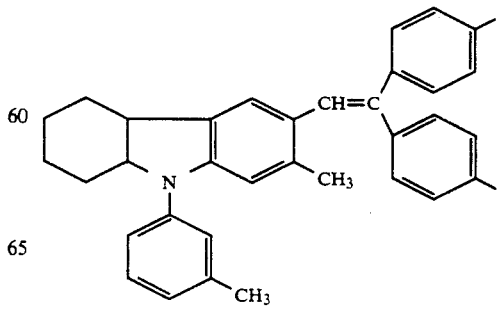 (IV-20)

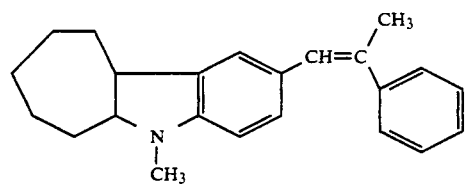 (IV-21)
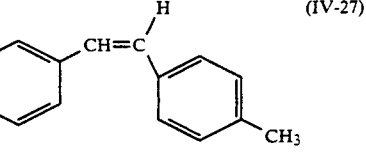 (IV-27)
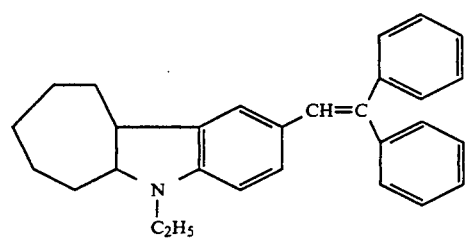 (IV-22)
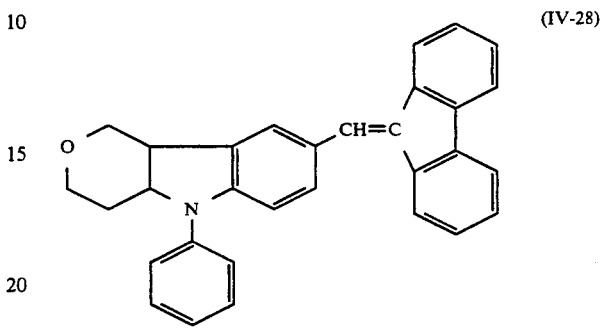 (IV-28)
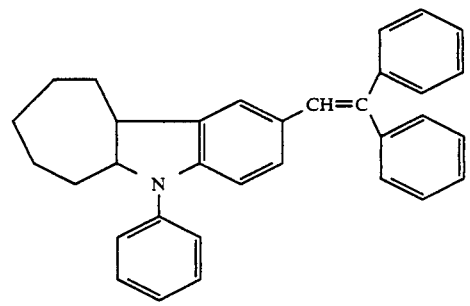 (IV-23)
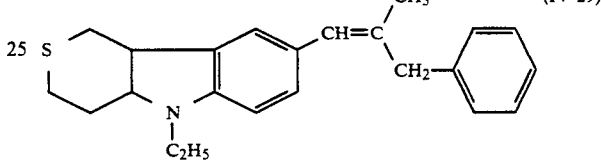 (IV-29)
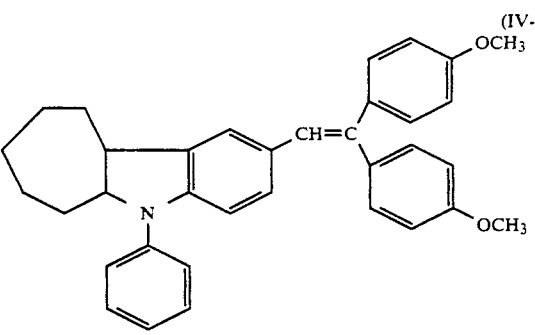 (IV-24)
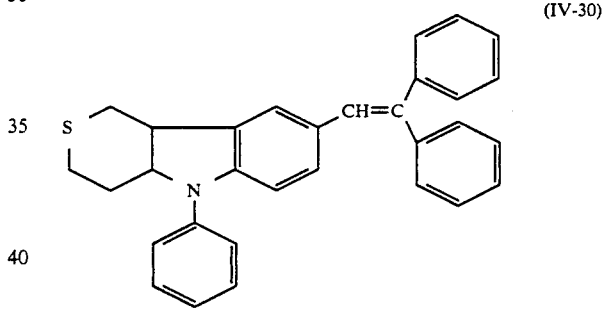 (IV-30)
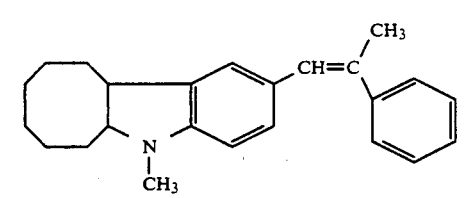 (IV-25)
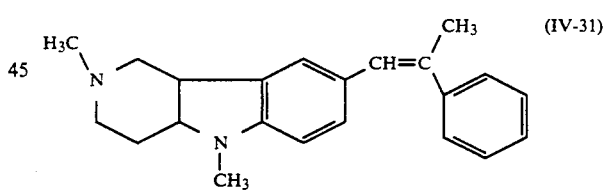 (IV-31)
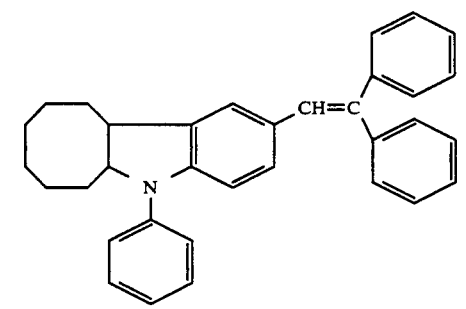 (IV-26)
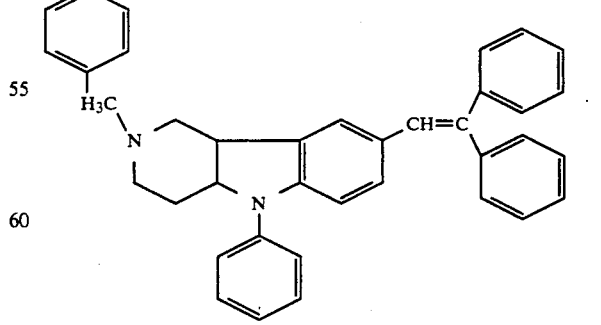 (IV-32)
These compounds represented by the formula (IV) can be prepared by the following process of preparation example.

PREPARATIVE EXAMPLE

[Preparation of the Above Compound (IV-3)]

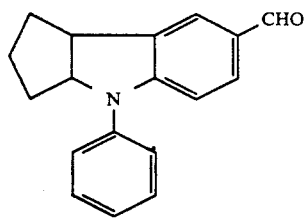

Potassium t-butoxide (1.46 g) was added to 1,2-dimethoxyethane solution (25 ml) of aldehyde compound of the above formula (3.31 g) and diethylbenzhydryl phosphonate (3.95 g) at 0° C. This was stirred at 0° C. for 20 minutes and further at room temperature for 1 hour and then the reaction mixture was introduced into water, followed by extraction with ethyl acetate. The product was purified by silica gel column chromatography to obtain 3.63 g of compound (IV-3).

m.p. 131.1°–132.7° C.
[NMR (δ, ppm, CDCl$_3$)
1.5–2.1 (m, 6H)
3.74 (m, 1H)
4.83 (m, 1H)
6.84 (s, 1H)
6.9–7.1 (m, 4H)
7.3–7.6 (m, 15H)

Examples of hydroquinone compounds represented by the formula (II) are shown below, but the present invention is never limited to use of them only.

| | |
|---|---|
| Hydroquinone | (II-1) |
| Methylhydroquinone | (II-2) |
| Phenylhydroquinone | (II-3) |
| Methoxyhydroquinone | (II-4) |
| Chlorohydroquinone | (II-5) |
| t-Butylhydroquinone | (II-6) |
| 2,5-Di-t-butylhydroquinone | (II-7) |
| n-Pentadecylhydroquinone | (II-8) |
| 2,5-Di-t-octylhydroquinone | (II-9) |

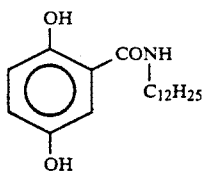 (II-10)

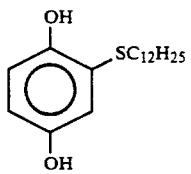 (II-11)

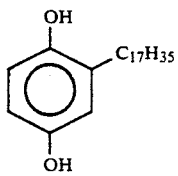 (II-12)

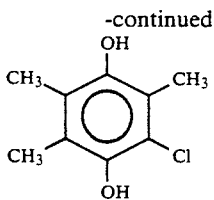 (II-13)

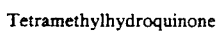 Tetramethylhydroquinone (II-14)

(II-14) Tetramethylhydroquinone

The hydroquinone compounds represented by the formula (II) are used in an amount of 0.01–50 parts by weight, preferably 0.01–10 parts by weight per 100 parts by weight of the carrier transport material.

Examples of the compounds represented by the formula (III) are shown below, but the present invention is never limited thereto.

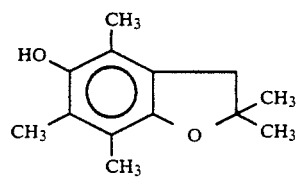 (III-1)

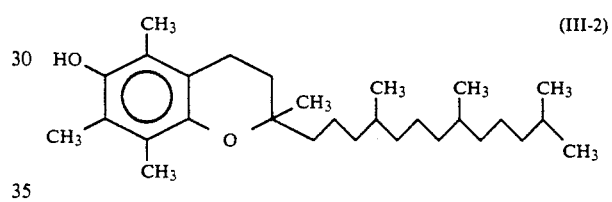 (III-2)

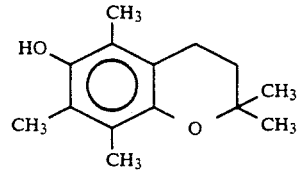 (III-3)

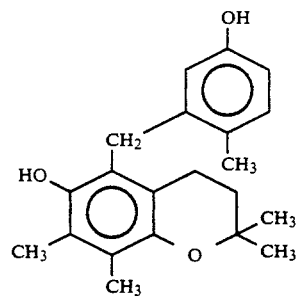 (III-4)

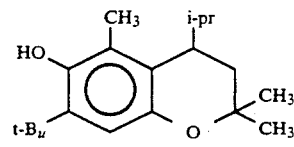 (III-5)

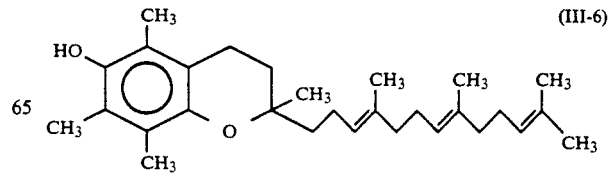 (III-6)

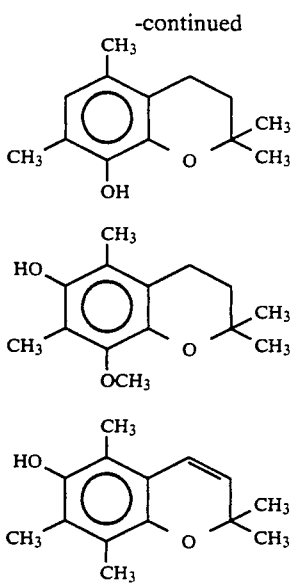

The compounds represented by the formula (III) are used in an amount of 0.01-50 parts by weight, preferably 0.01-10 parts by weight per 100 parts by weight of the carrier transport material.

At least one of the compounds represented by the formula (II) and at least one the compounds represented by the formula (III) are used.

Thickness of carrier transport layer is preferably about 5-100 μm.

Photosensitive layer of the electrophotographic photoreceptor may contain known plasticizer in order to improve film-formability, flexibility and mechanical strength. The plasticizer includes, for example, aromatic compounds such as phthalic esters, phosphoric esters, epoxy compounds, chlorinated paraffins, chlorinated fatty acid esters, and methylnaphthalene.

Furthermore the photoreceptor of the present invention may have adhesive layer, intermediate layer and transparent insulation layer, if necessary.

The following nonlimiting examples explain the present invention in more detail.

EXAMPLE 1

0.2 g of a compound represented by the following formula (VI) and 0.2 g of a phenoxy re in (PKHJ manufactured by UCC) were added to 20 ml of tetrahydrofuran and were dispersed by a paint shaker for 2 hours. The resulting dispersion was coated on an Al-vapor deposited PET film conductive support (METALUMY manufactured by Panack Kogyo Co.) and dried to form a carrier generation layer of 0.2 μm thick.

Furthermore, 100 g of the above exemplified compound (I-a-4) as a hydrazone, 100 g of a polyarylate resin (U-100 manufactured by Unitika, Ltd.), 2.0 g of t-butylhydroquinone (II-6) and 2.0 g of the above exemplified compound (III-2) (α-tocopherol) were dissolved in 1300 g of methylene chloride. This solution was coated on the carrier generation layer and dried to form a carrier transport layer of 24 μm thick. Thus, an electrophotographic photoreceptor was obtained.

This photoreceptor was kept in the dark at room temperature for 24 hours and thereafter, the photoreceptor was charged at a charging voltage of −4.8 KV by an electrostatic recording paper testing machine SP-428 (manufactured by Kawaguchi Denki Co., Ltd.) and charge quantity was measured.

Then, the surface of the photoreceptor was exposed to light of a fluorescent lamp of 5000 lux for 5 minutes and then the photoreceptor was again charged under the same charging condition as above and charge quantity was measured. Ratio in percentage of charge quantities before and after exposure to light was calculated and this was employed as characteristic value of pre-exposure.

Separately, changes in initial potential and residual potential due to repetition of 10000 times of a cycle of charging, exposing and charge elimination were measured by a surface electrometer 344 (manufactured by Treck Co.) in a copying machine SP-8100 (manufactured by Sharp Corporation) from which development unit was removed. The results are shown in Table 3.

EXAMPLE 2-9

Photoreceptors were produced in the same manner as in Example 1 except that addition amounts of t-butylhydroquinone and α-tocopherol were as shown in Table 1 and characteristics thereof were measured as in Example 1. The results are shown in Table 3.

TABLE 1

| Addition amounts of t-butylhydroquinone and α-tocopherol in Examples 1-9. | | |
|---|---|---|
| | t-Butylhydroquione | α-Tocopherol |
| Example 1 | 2.0 g | 2.0 g |
| Example 2 | 1.0 g | 2.0 g |
| Example 3 | 0.5 g | 2.0 g |
| Example 4 | 2.0 g | 1.0 g |
| Example 5 | 1.0 g | 1.0 g |
| Example 6 | 0.5 g | 1.0 g |
| Example 7 | 2.0 g | 0.5 g |
| Example 8 | 1.0 g | 0.5 g |
| Example 9 | 0.5 g | 0.5 g |

COMPARATIVE EXAMPLES 1-7

Photoreceptors were produced in the same manner as in Example 1 except that addition amounts of t-butylhydroquinone and α-tocopherol were as shown in Table 2

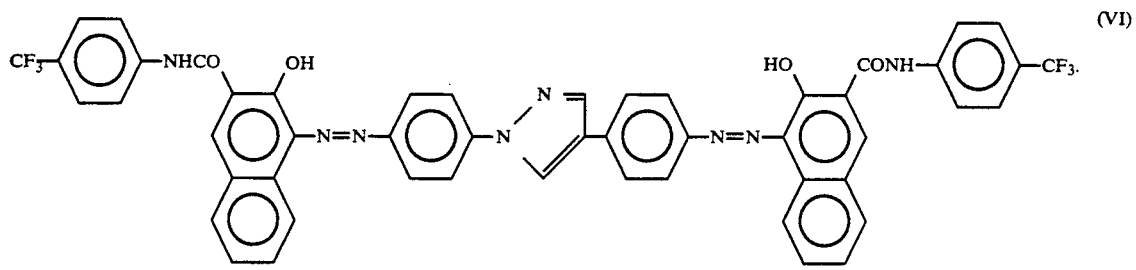

and characteristics thereof were measured. The results are shown in Table 3.

TABLE 2

Addition amounts of t-butylhydroquinone and α-tocopherol in Comparative Examples 1–7.

| | t-Butylhydroquione | α-Tocopherol |
|---|---|---|
| Comparative Example 1 | Not added | Not added |
| Comparative Example 2 | " | 0.5 g |
| Comparative Example 3 | " | 1.0 g |
| Comparative Example 4 | " | 2.0 g |
| Comparative Example 5 | 0.5 g | Not added |
| Comparative Example 6 | 1.0 g | " |
| Comparative Example 7 | 2.0 g | " |

EXAMPLE 10

The photoreceptor produced in Example 1 was left to stand in the dark under constant temperature and humidity of 50° C. and 80% RH for 3 days, 7 days and 14 days and changes in initial potential and residual potential after repetition of 10000 times of the cycle of the electrophotographic process as in Example 1 were measured. The results are shown in Table 4.

EXAMPLES 11–14

The photoreceptors produced in Examples 2, 3, 5 and 6 were left to stand in the dark under constant temperature and humidity of 50° C. and 80% RH for 3 days, 7 days and 14 days and changes in initial potential and residual potential after repetition of 10000 times of the cycle as in Example 1 were measured. The results are shown in Table 4.

COMPARATIVE EXAMPLE 8

The photoreceptor produced in Comparative Example 1 was left to stand in the dark under constant temperature and humidity of 50° C. and 80% RH for 3 days, 7 days and 14 days and changes in initial potential and residual potential after repetition of 10000 times of the cycle as in Example 1 were measured. The results are shown in Table 4.

COMPARATIVE EXAMPLES 9–11

The photoreceptors produced in Comparative Examples 2, 3 and 4 were left to stand in the dark under constant temperature and humidity of 50° C. and 80% RH for 3 days, 7 days and 14 days and changes in initial potential and residual potential after repetition of 10000 times of the cycle as in Example 1 were measured. The results are shown in Table 4.

EXAMPLE 15

A photoreceptor was produced in the same manner as in Example 1 except that 2.0 g of n-pentadecylhydroquinone was used in place of t-butylhydroquinone. This photoreceptor was left to stand in the dark for 24 hours and then, pre-exposure characteristics and characteristics after repetition of 10000 times of the cycle as in Example 1 were measured. Furthermore, this photoreceptor was left to stand in the dark at 50° C. and 80% RH for 3 days, 7 days and 14 days and pre-exposure characteristics and characteristics after repetition of 10000 times of the cycle were also measured. The results are shown in Table 4.

COMPARATIVE EXAMPLE 12

A photoreceptor was produced in the same manner as in Example 1 except that α-tocopherol was not added and 2.0 g of n-pentadecylhydroquinone was added. Pre-exposure characteristics and characteristics after repetition of the cycle were measured. The results are shown in Table 3.

TABLE 3

Pre-exposure characteristics and repetition characteristics

| | Pre-exposure characteristics (5000 LUX · 5 min) [%] (1) | Repetition characteristics (V) (10000 times) | |
|---|---|---|---|
| | | Change in initial potential | Change in residual potential |
| Example 1 | 83 | −25 | +30 |
| Example 2 | 80 | −37 | +22 |
| Example 3 | 81 | −42 | +12 |
| Example 4 | 79 | −20 | +52 |
| Example 5 | 80 | −20 | +37 |
| Example 6 | 78 | −27 | +28 |
| Example 7 | 75 | −15 | +75 |
| Example 8 | 76 | −22 | +63 |
| Example 9 | 75 | −30 | +58 |
| Comparative Example 1 | 62 | −25 | +89 |
| Comparative Example 2 | 61 | −37 | +55 |
| Comparative Example 3 | 62 | −55 | +15 |
| Comparative Example 4 | 59 | −78 | +2 |
| Comparative Example 5 | 67 | −15 | +92 |
| Comparative Example 6 | 75 | +2 | +105 |
| Comparative Example 7 | 85 | +10 | +133 |
| Comparative Example 12 | 86 | +25 | +127 |

(1) $\frac{\text{Quantity of charge after exposure}}{\text{Quantity of charge before exposure}} \times 100$

TABLE 4

Change of repetition characteristics under 50° C., 80% RH.

| | At start (3) | | After 3 days | | After 7 days | | After 14 days | |
|---|---|---|---|---|---|---|---|---|
| | ΔVo (1) | ΔVr (2) | ΔVo | ΔVr | ΔVo | ΔVr | ΔVo | ΔVr |
| Example 10 | −25 | +30 | −24 | +28 | −27 | +31 | −22 | +30 |
| Example 11 | −37 | +22 | −30 | +25 | −35 | +20 | −35 | +20 |
| Example 12 | −42 | +12 | −47 | +15 | −50 | +15 | −39 | +18 |
| Example 13 | −20 | +37 | −20 | +35 | −18 | +30 | −18 | +35 |
| Example 14 | −27 | +28 | −25 | +25 | −25 | +25 | −22 | +29 |
| Comparative Example 8 | −25 | +89 | −30 | +98 | −35 | +108 | −40 | +130 |
| Comparative Example 9 | −37 | +55 | −36 | +62 | −35 | +68 | −29 | +85 |

TABLE 4-continued

| | Change of repetition characteristics under 50° C., 80% RH. | | | | | | | |
|---|---|---|---|---|---|---|---|---|
| | At start (3) | | After 3 days | | After 7 days | | After 14 days | |
| | ΔVo (1) | ΔVr (2) | ΔVo | ΔVr | ΔVo | ΔVr | ΔVo | ΔVr |
| Comparative Example 10 | −55 | +15 | −50 | +18 | −42 | +26 | −30 | +55 |
| Comparative Example 11 | −78 | +2 | −72 | +4 | −49 | +25 | −25 | +55 |
| Example 15 | −45 | +15 | −65 | +18 | −47 | +18 | −49 | +21 |

(1) Difference in initial potential after repetition of 10000 times of the cycle of electrophotographic process.
(2) Difference in residual potential after repetition of 10000 times of the cycle of electrophotographic process.
(3) The same value as in Table 3.

EXAMPLE 16

Example 1 was repeated except that stilbene compound (IV-3) was used in place of hydrazone compound (I-a-4) as carrier transport material. The results are shown in Tables 6 and 7.

COMPARATIVE EXAMPLES 13-15

Example 16 was repeated except that addition amounts of t-butylhydroquinone (II-6) and α-tocopherol (III-2) were as shown in Table 5. The results are shown in Tables 6 and 7.

TABLE 5

| Addition amounts of t-butylhydroquinone and α-tocopherol in Example 16 and Comparative Examples 13-15. | | |
|---|---|---|
| | t-Butylhydroquione | α-Tocopherol |
| Example 16 | 2.0 g | 2.0 g |
| Comparative Example 13 | Not added | Not added |
| Comparative Example 14 | 2.0 g | Not added |
| Comparative Example 15 | Not added | 2.0 g |

TABLE 6

| Results of measurements of pre-exposure characteristics and characteristics after repetition. | | |
|---|---|---|
| | Pre-exposure characteristics (5000 LUX · 5 min) [%] | Characteristics after repetition of 1000 times (V) |
| | | Change in initial potential | Change in residual potential |
| Example 16 | 78 | −72 | +20 |
| Comparative Example 13 | 55 | −180 | +95 |
| Comparative Example 14 | 72 | −105 | +150 |
| Comparative Example 15 | 60 | −180 | +18 |

TABLE 7

| | Change in repetition characteristics at 50° C. and 80% RH. | | | | | | | |
|---|---|---|---|---|---|---|---|---|
| | At start | | After 3 days | | After 7 days | | After 14 days | |
| | ΔVo | ΔVr | ΔVo | ΔVr | ΔVo | ΔVr | ΔVo | ΔVr |
| Example 16 | −72 | +20 | −65 | +22 | −65 | +23 | −63 | +25 |
| Comparative Example 13 | −180 | +95 | −205 | +105 | −210 | +125 | −195 | +155 |
| Comparative Example 14 | −105 | +150 | −100 | +145 | −120 | +145 | −120 | +180 |
| Comparative Example 15 | −180 | +18 | −200 | +35 | −190 | +45 | −180 | +65 |

The electrophotographic photoreceptors of the present invention are stable in characteristics after repeated use as can be seen from Table 3 and are excellent in storage stability as can be seen from Table 4.

What is claimed is:

1. A double-layered type electrophotographic photoreceptor which comprises an electroconductive support and a carrier generation layer containing a pigment or a dye as a carrier generation material and a carrier transport layer which are provided on said support, wherein the carrier transport layer contains an organic low molecular weight carrier transport material, a binder resin, a hydroquinone compound represented by the following formula (II):

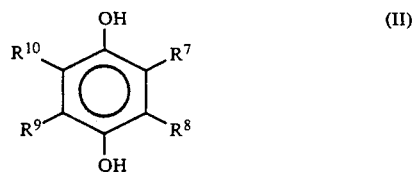

wherein $R^7$, $R^8$, $R^9$ and $R^{10}$ each represents a hydrogen atom, a halogen atom, an alkyl group, an aryl group, an alkoxy group, a carbamoyl group or an alkylthio group, and a compound represented by the following formula (III):

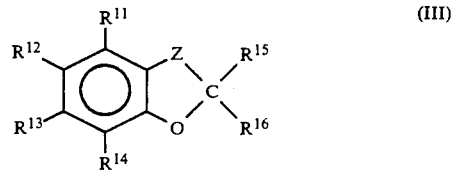

wherein $R^{11}$, $R^{12}$, $R^{13}$ and $R^{14}$ each represents a hydrogen atom, a hydroxyl group, an alkyl group or an alkoxy group with a proviso that at least one of $R^{11}$–$R^{14}$ is hydroxyl group, $R^{15}$ and $R^{16}$ each represents a hydrogen atom, an alkyl group or an alkenyl group and Z represents a group of atoms necessary to form a 2H-chromene skeleton, chroman skeleton or dihydrobenzofuran skeleton together with the benzene ring in the formula and the group of atoms may be further substituted.

2. A photoreceptor according to claim 1, wherein the carrier transport layer contains 0.1-10 parts by weight of the compound represented by the formula (II) and 0.1-10 parts by weight of the compound represented by the formula (III) per 100 parts by weight of the carrier transport material.

3. A photoreceptor according to claim 1, wherein the carrier transport material is a hydrazone compound or a stilbene compound.

4. A photoreceptor according to claim 1, wherein the carrier transport material is a compound represented by the following formula (I-a) or (I-b):

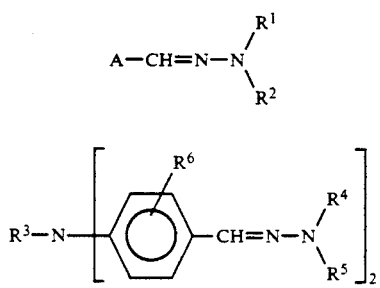

wherein $R^1$, $R^2$, $R^3$, $R^4$, and $R^5$ each represents an alkyl, alkenyl, aralkyl, aryl or heterocyclic group which may be substituted, $R^6$ represents a hydrogen atom, an alkyl group, an alkoxy group or a halogen atom, and A represents an aromatic hydrocarbon or aromatic heterocyclic group which may have substituent.

5. A photoreceptor according to claim 1, wherein the carrier transport material is a compound represented by the following formula (IV):

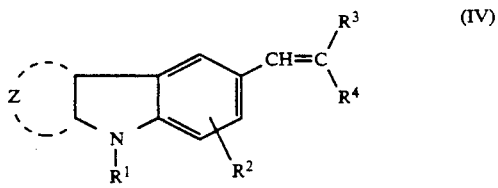

wherein $R^1$, $R^2$, $R^3$, and $R^4$ each represents a hydrogen atom or an alkyl, aralkyl, or aryl group which may have substituent, $R^3$ and $R^4$ may link to each other to form a ring, and Z represents a group of atoms necessary to form a saturated 5-8 membered ring together with the two carbon atoms of indoline ring.

6. A photoreceptor according to claim 1, wherein the carrier transport layer contains 20-500 parts by weight of the carrier transport material per 100 parts of the binder resin.

* * * * *